United States Patent
Gray et al.

(10) Patent No.: US 7,691,417 B2
(45) Date of Patent: Apr. 6, 2010

(54) TUMOR AND MUTATION SUPPRESSING PLANT EXTRACT

(75) Inventors: Sandra L. Gray, Seneca, SC (US); N. Dwight Camper, Clemson, SC (US)

(73) Assignee: Clemson University Research Foundation, Anderson, SC (US)

( * ) Notice: Subject to any disclaimer, the term of this patent is extended or adjusted under 35 U.S.C. 154(b) by 1138 days.

(21) Appl. No.: 11/217,209

(22) Filed: Sep. 1, 2005

(65) Prior Publication Data

US 2006/0045922 A1 Mar. 2, 2006

Related U.S. Application Data

(60) Provisional application No. 60/606,657, filed on Sep. 2, 2004.

(51) Int. Cl.
  *A01N 65/00* (2006.01)

(52) U.S. Cl. .................. 424/725; 424/773; 424/774
(58) Field of Classification Search ................ None
  See application file for complete search history.

(56) References Cited

U.S. PATENT DOCUMENTS

| 4,263,286 | A | 4/1981 | Nakajima et al. |
| 5,041,425 | A | 8/1991 | Hasegawa et al. |
| 5,567,425 | A | 10/1996 | Bathurst et al. |
| 6,004,558 | A | 12/1999 | Thurn et al. |
| 6,008,260 | A | 12/1999 | Pezzuto et al. |
| 6,656,729 | B2 | 12/2003 | Bathurst et al. |

*Primary Examiner*—Michele C. Flood
(74) *Attorney, Agent, or Firm*—J. Bennett Mullinax, LLC

(57) ABSTRACT

A compound derived from an extract of vegetative tissue of plants of the Genus *Shortia* demonstrates antitcarcinogenic potential by inhibiting the growth and development formation of tumors in living tissue in response to an organism known to cause the initiation of tumors in living tissue and by reducing mutation rates in living tissues exposed to a known mutagen.

2 Claims, No Drawings

TUMOR AND MUTATION SUPPRESSING PLANT EXTRACT

This application claim priority of U.S. Provisional Patent Application No. 60/606,657 filed Sep. 2, 2004.

TECHNICAL FIELD

This invention relates to extracts of naturally occurring materials capable of suppressing tumor formation and growth, and mutation. More specifically it relates to plant extracts that inhibit tumors induced by proliferation factors in a plant tissue model system of tumor genesis and that display tumor inhibiting activity. Because of common biological processes involved in cell proliferation and tumor growth shared by both plant and animal tissues and in mutagenesis, the extract, hence the invention, is also relevant to tumor suppression in animal tissue.

BACKGROUND OF THE INVENTION

Regulation of cell proliferation in both normal and tumorous tissue remains of fundamental scientific interest and clinical significance in the prevention and treatment of various types of diseases, particularly cancer and related diseases. In animals, including humans, many of the diseases are recognized as some form of malignant cancer. Plants produce tumor-like growths in response to a variety of stimuli, including certain microorganisms. Because the similarity of animals and plants of basic biological process involved with tumor initiation and growth, materials that affect tumor growth in plants are of more than casual interest in the potential treatment of cancer in humans. Genetic mutations are also recognized as playing significant roles in tumor formation and growth.

In addition to interest in materials that uniquely affect tumor formation in plants, in recent years, clinical and basic interest in potential antitumor properties in animals of a wide range of plant extracts has accelerated dramatically. A significant force in this accelerated interest is recognition of the roles diet plays in both the cause of and prevention of cancer in humans. See, for example, M. B. Sporn, Fed. Proc., 38, 2528 (1979).

Dietary management can significantly affect the risk of developing cancer. Increasingly, plant materials found in common dietary constituents have proved to have antitumor (or anti-cancer) properties. Unfortunately, the opposite is also apparently true, certain plant extracts are known to cause or increase the risk of the development of cancer in humans. Ideally, the human diet should be modified to minimize exposure to dietary carcinogens while simultaneously optimizing intake of cancer preventive agents. Progress towards this condition requires identification of both causative and preventative agents that occur in the human diet.

Plants and plant extracts have long been recognized as having great potential medicinal value. As early as 1500 B.C., *The Papyrus Ebers*, an ancient Egyptian medical text, recognized over 700 herbal remedies. Records suggest the practice of herbal medicine in Chinese culture as early as 2500 B.C. Native Americans, as cited in numerous sources, effectively used herbals as medicines in addition to related rituals. In first U.S. Pharmacopoeia published in 1820 lists 296 substances, of which 130 were "medicines" used by Native Americans.

The plant kingdom is enormous and diverse and largely unstudied with respect to potential medicinal value. In spite of the historic use of plans and plant extracts, only from 5 to 15% of the 250,000 species of higher plants have been chemically and pharmacologically evaluated for potential medicinal value.

Plant materials, including extracts from various tissues, have been used to treat a variety of conditions and have been recognized as appropriate material for protection under U.S. patent law. For example, U.S. Pat. No. 4,263,286 issued to T. Nakajima, et al. on Apr. 21, 1981 claims a method for treating a wide array of disorders with a soybean (*Glycine max* L) extract. The '286 patent claims a method of treating consciousness disorders with appropriate doses of phosphatidylcholines (a form of lecithin) with excellent biological activity purified from soy bean plants.

More recently, emphasis has been placed on plant extracts displaying anticarcinogen or cancer chemotherapeutic properties.

U.S. Pat. No. 5,041,425, issued Aug. 20, 1991 to Hasegawa and Lam discloses the use of citrus extracts (limononds) in treating cancer, particularly gastric cancers. The compound reduced induced tumors in mice by 28%, from 100% to 72%. The suggested mode of action was increased antitumor enzymatic activity.

Cancer therapeutic compounds from plants are the subject of other patents. U.S. Pat. No. 6,004,558, titled Method for Treating Cancer with Legume Plant Extracts, issued Dec. 21, 1999 to Thurn and Huang discloses and claims the use of purified extracts of materials derived from various legumes. Tests were conducted on free-cell extracts and on a prostate cancer patient using extracts from legumes from which specific isoflavones (genistein, daidzein, formononetin, and biochanin, and/or their glycosides) were removed. The cell-free tests equate anti-carcinogenic potential in part with reduced cell proliferation, and apoptosis, DNA fragmentation, and growth inhabitation. The efficiency of the extract on prostate cancer was gauged by decreased PSA (prostate specific antigen) level in response to treatment with the extract.

Cyclooxygenase is a metabolic enzyme intermediary involved in stimulating tumor growth. Cancer chemopreventive agents include non-steroid, anti-inflammatory drugs that inhibit cyclooxygenase. Extracts derived from *Cassia quinquangulata* Rich (Leguminosae) are identified in U.S. Pat. No. 6,008,260, Titled Cancer Chemopreventative Composition and Method issued Dec. 28, 1999 to Pezzuro et. al. The active agent identified in the '260 patent is resveratrol for which the molecular configuration is presented.

The regulation of apoptosis has been associated with anti-carcinogens. See, U.S. Pat. No. 5,567,425, title Compositions Which Inhibit Apoptosis, Methods of Purifying the Compositions and Uses Thereof, issued Oct. 22, 1996 to Bathurst et al. The '425 patent discloses materials with apoptosis-regulating abilities derived from plants of at least three families—legumes, nightshade, and garlic. Without reference to antitumor or anticarcinogenic potential, the claims relate to compositions that inhibit normal cell death (antia-apoptic) action. U.S. Pat. No. 6,656,729, with the same title and inventors as the '425 patent which traces to U.S. patent application Ser. No. 08/158,980. Both the '425 and the '729 patents focus on preventing apoptosis using at least one phytogenic inhibitor.

There remains room for detecting and isolating anti-tumor and anti-mutagenic materials in a wider array of taxa of higher plants, for determining the nature of antitumor action, and for characterizing compositions that induce antitumor reactions in tissues.

SUMMARY OF THE INVENTION

A purpose of the invention is to extract anti-carcinogenic compounds from plants; an additional purpose is to extract anti-mutagenic compounds from the same plants, and a still further purpose of the invention is to evaluate plants of rare and exotic species indigenous to the Appalachian Mountains of the eastern United States for extracts with anti-carcinogenic or anti-mutagenic properties.

These and other purposes are satisfied by an invention in which vegetative parts of plants of the genus *Shortia* are extracted with an aqueous solution of alcohol, an organic solvent, or a non-organic solvent, and the extracted materials are tested for anti-carcinogenic and for anti-mutagenic properties.

The following detailed discussion of the invention including the appended claims provides comprehensive teaching as to a best mode to make and use the invention.

DETAILED DESCRIPTION OF THE INVENTION

The invention utilizes rapid and inexpensive bench-top bioassays for initial evaluation of the tumor suppressing properties of a plant extract by treating tissue that has been exposed to a known tumor-inducing agent with the extract and determining the level of suppression of tumor formation and/or growth. In a parallel assay, the effect of the extract on mutagenicity is estimated. Mutagenicity is known to be closely associated with carcinogenicity.

Tumor suppression is evaluated following the well-known *Agrobacterium* tumor induction assay procedure. The assay depends on the unique property of *Agrobacterium tumefaciens* of inserting a portion of its tumor-inducing (Ti) plasmid into the chromosomal DNA of a wounded plant, causing tumor-like growths on the plant, a condition commonly known to those skilled in the art as Crown Gall disease. Antitumor potential is measured by tumor suppression on aseptic potato discs treated with the plant extract. See A. B. Galsky, et al. J. Nat. Cancer Inst. 1981. 67:689-692, incorporated herein by reference, in its entirety. Antitumor activity detected by the *Agrobacterium* assay is correlated with suppression of tumors in animals; thus, plant extracts that suppress *Agrobacterium*-induced tumor formation have significant potential as human anticarcinogens.

Mutagenicity is evaluated following the Ames *Salmonella* mutagenic assay, a bacterial reverse mutation test using a histidine-dependent autotrophic mutant of *Salmonella typhimurium* lacking both normal DNA repair mechanisms and the ability to grow on a histidine-free medium. See, D. R. Maron and B. Ames. Mutation Research. 1980. 113:173-215, incorporated herein by reference in its entirety. As one skilled in the art understands, the test assumes that DNA-altering chemicals cause mutations and that mutagenicity is closely associated with carcinogenicity. Induced mutations are estimated by the number of bacteria capable of growing on a histidine-free medium.

Plant Extract

All extracts were made from vegetative material (leaves and rhizomes) of *Shortia galacifolia* T.&G., Diapensiaceae, commonly recognized as "Oconee Bell." Materials were collected in the winter (dormant season) from native populations in Oconee County, S.C., and from transplanted populations at the South Carolina Botanical Garden, Clemson, S.C. Species identification was verified professionally by the Clemson University Herbarium (Clemson University, Herbarium identification #63415, Clemson, S.C.).

Extracts were made as follows:
Plant samples were washed for 5 minutes under running tap water and dried at room temperature (approximately 20 C or 68 F) overnight.
Materials were divided into one of three categories: leaf material, new growth rhizomes, and mature rhizomes and dried in an oven at 40 C (104 F) for 48 hours.
Approximately 5 g of dried sample were ground to a fine powder.
Crude extracts of plant material were prepared by mixing 1-g aliquots of the powdered material with 8 ml of 80% methanol and agitating on a lateral shaker for 8 hours at room temperature (approximately 20 C, 68 F). Samples are then centrifuged at 1800×g for 20 minutes and the supernatant saved.
The residual pellet from this centrifugation was extracted following the preceding procedure. The supernatants from the two centrifugations were combined and evaporated to dryness at 40° C. (approximately 104 F) under a gentle flow of filtered air. Samples were reconstituted to a 1 g/ml concentration with 100% ethanol or with dimethyl sulfoxide (DMSO). The reconstituted samples are filtered with a 0.45 µm membrane disk filter (Versapor Acrodisc ®, V45W500, Pall Gelman, Ann Arbor, Mich.) to remove particulate matter and finally were stored at 4 C (approximately 39 F) in the dark until used.
The preceding extraction was modified using 100% hexane or 80% methanol for extractions and dilute DMSO for testing.

Antitumor Assay Methods

Antitumor effects of extracts were tested using the Potato Tumor Induction method of McLaughlin's laboratories. 1 *A. tumefaciens* was cultured in Difco Yeast Extract Medium for a period of 48-72 hours at 28° F. (approximately 118 F) for use in the assay.

Test tissue was prepared from organically grown, red-skinned potatoes (*Solanum tuberosum* L., Solanaceae) as follows:
Tubers were washed under running tap water and surface sterilized with a 0.6% sodium hypochlorite solution for 20 minutes.
A thin slice was cut from each side of the tuber to produce flat, peeled surfaces.
The tubers next were sterilized by immersion in a 1.2% sodium hypochlorite solution for 15 minutes.
Cores of tissue were aseptically cut from each tuber using a #9 (11 mm) cork borer. The cylinders of tissue were rinsed twice in distilled water adjusted to pH 40, and pieces approximately 2 cm in length are cut from each end of this cylinder and discarded. The remainder of the cylinder is cut into 0.5 cm discs.
Potato discs were rinsed in sterile water and transferred to a well-culture plate; a 24-well culture plate (Corning Costar ®, Model 3524, Cambridge, Mass.) is appropriate, but not a limitation. The well-culture plate was prepared with 1.5 ml water agar (1.5%) per well.
An *A. tumefaciens* suspension was prepared by adding 7-10 loops of cultured bacteria to 15 ml phosphate buffered saline (PBS, pH7.2) until obtaining an absorbance value of 0.96±0.2 at 600 nm, which corresponds to approximately $1 \times 10^9$ colony forming units.
The assay included three controls. Camptothecin (Cat. No. C9911; Sigma Chemical; Saint Louis, Mo.), a known anti-mitotic, anti-neoplastic agent was added to discs inoculated with *A. tumefaciens* as positive inhibitory control. Plant extracts were diluted with 50% ethanol; thus, *A. tumefaciens* inoculated disks treated with a 50% ethanol solution were a positive control for tumor inhibition by 50% ethanol. A solvent control using 50% ethanol added to discs not inoculated with *A. tumefaciens* tested for solvent induced tumor formations.

Samples were prepared as follows:

All reagents controls and plant extracts were filter-sterilized (0.2 um HT Tuffryn® Acrodisc®, Syringe Filter, Pall Gelman, Model 4192, Ann Arbor, Mich.).

The positive inhibitory control contained 600 µl camptothecin stock (100 µg/ml)+150 µl sterile distilled water+ 750 µl *A. tumefaciens* stock;

The positive control had control had 600 µl 50% ethanol, 150 µl sterile distilled water+750 µl *A. tumefaciens* stock;

For the solvent control, PBS replaced the *A. tumefaciens* stock;

Test samples contained 600 µl dilute plant extract, 150 µl sterile distilled water+750 µl *A. tumefaciens*, Potato discs on water agar were overlaid with 50 µl of these solutions.

Two culture plates with 12 discs per plate were used for each combination, for a total of 24 replicates per combination.

Plates were incubated in the dark at room temperature (20 C or 68 F) for 14 days. Discs were stained with Lugol's Potassium Iodide Reagent to facilitate tumor detection. See, N. R. Ferrigni, et al. 1982. 45: 679-686. to facilitate tumor detection.

Tumors on each stained potato disc were counted with the aid of a dissecting microscope. Total number of tumors on control discs was compared with the total on extract treated discs and percent tumor inhibition calculated, Table 1.

The *Shortia* extract (1 g/ml) was diluted in 50% ethanol to obtain four concentrations thereby evaluating the effects of extract concentration on tumor suppression, Table 1. Dilutions were 10 mg/ml (1:100), 1 mg (ml (1:1000), 0.1 mg/ml (1:10,000), and 0.10 mg/ml (1:100,000). As previously described, comparisons included three controls and the dilutions in two culture dishes of 12 discs, each for a total of 24 replications. The entire assay was repeated three times.

EXAMPLE 1

Tumor Suppression

Overall, an extract from vegetative material of plants of *Shortia galacifolia* T.&G. suppressed tumor formation in discs of potatoes induced by *A. tumefaciens*. Appropriate controls confirm that the detected tumor suppression is not an artifact, nor is it a product of tissue preparation protocol or a response to any solvent or combinations of solvents.

The assay results illustrating the effects of concentrations of a plant extract derived from different tissues of *Shortia galacifolia* are summarized in Table 1 in which 'Cont' is the positive control in which only the tumor inducing agent, *A. tumefaciens* was added, and no tumor suppression observed, as would be anticipated. (The positive, camptothecin control resulted in effectively complete (98.2%) tumor inhibition resulting from effects on the tumor inducing agent, *A. tumefaciens*, and as anticipated, the 50% ethanol control, absent the inducing agent had no effect.) 'LF' in Table 1 indicates leaf tissue as a source of the extract, 'NRh' new rhizome tissue, and 'MRh' mature rhizome tissue as the source of the extract. Dilutions are 50% ethanol dilutions of each extract source. The % Tumor Inhibition was calculated as % inhibition=(control mean)−(extract mean)×100/ (control mean)

From Table 1, clearly the extract suppressed tumor formation compared with the positive control, Cont. overall extract from mature rhizomes suppressed tumors more than extracts from either leaves or new rhizomes, which were essentially comparable, 81.8% suppression vs 69.9 and 70.0%.

Generally higher concentrating (lower dilution) of the extract produced greater inhibition. Although statistically significant, average concentration differences appeared to be of lesser practical significance because of the potential effects of a tissuexconcentration interaction that did not alter the fundamental finding of effectiveness of the extract in tumor suppression.

In independent, parallel studies, rhizome extracts were made with both hexane and 80% methanol. In these studies, dilution effects were more pronounced, Table 2. The solvents hexane and methanol (80%) were equally effective at the highest concentration (10 mg/ml), 63.4% and 63.8% inhibition, respectively, and effectiveness decreased with both reagents more than with ethanol, Table 1.

From Tables 1 and 2, it is clear that an extract from vegetative parts of plants of *Shortia galacifolia* suppress tumors induced by *A. tumefaciens* in potatoes. Because of the biological similarities between tumor growth in plant tissues, such as tubers, and in certain animal tissues, as one skilled in the art recognizes, parallel tumor suppression by such extracts on animal tissue is anticipated by the invention.

Antimutagenic Assay Methods

Antimutagenic effects of extracts were assayed by the Ames *Salmonella*/microsome mutagenic test with modifications. See D. R. Maron and B. Ames. Mutation Research. 1980. 113:173-215 and K. Mortelmans and E. Zeiger. Mutation Research. 2000. 455:229-260 both of which are herein incorporated by reference in their entirety. Extracted plant samples were diluted 1:1000 with DMSO. Master plates were prepared from stock cultures of *Salmonella typhimurium* (Strain TA 100, Xenometrix, San Diego, Calif.).

Colonies chosen to generate overnight cultures were grown in 5 ml nutrient broth #2 (Cat No. CM 0067; Oxid Products; Basingstone, Hampshire, UK) at ° C. to a density of $1-2\times10^9$ per ml (absorbance of 0.96±0.2 at 600 nm). Cells were diluted 1:10 prior to use in tests.

The assay consisted of combining either controls or the test compound and the *Salmonella* tester strain the mutagen, S9 liver microsomes in a soft top agar poured onto a minimal agar plate lacking histidine. Top agar (0.6% noble agar and 0.5% sodium chloride) was melted and 10 ml mM/L-histidine. HCl/0.5 mM biotin was added to 100 ml agar.

Twenty ml of human S9 mix (Moltox™; Product 14-102; Boone, N.C.) {8 mM $MgCl_2$, 33 mM KCL, 5 mM glucose-phosphate, 4 mM nicotinamide adenine dinucleotide phosphate (NADP), 100 mM sodium phosphate, pH 7.4 and 0.04 ml S9} were prepared immediately before assay. The S9 mix was divided into four 4 ml portions each of which had one of the following added: 10.4 µl DMSO, 10.4 µl leaf extract, 10.4 µl new growth rhizome extract, or 10.4 µl nature rhizome extract.

Test compounds with the S9 mix were incubated for 30 minutes at 37° C., filter sterilized (0.2 µm Acrodisc® V45W500; Pall Galman, Ann Arbor, Mich.), and divided into two 1.5 ml duplicate aliquots. One aliquot of each duplicate set was treated with 6 µl (1 mg/ml) of the mutagen 2-aminianthuracene (2-AA) [CAS no. 613-13-8], and the second had 6 μl DMSO added and served as a control for each treatment. All aliquots were incubated 30 min at 37° C. Each aliquot was divided into three 500 μl portions in plastic culture tubes, and 100 μl *Salmonella typhimurium* dilution and 2 ml molten top agar was added to each tube. Each aliquot was vortexed briefly and immediately poured on Petri dishes containing the minimal glucose agar (MGA) which were allowed to solidify, then inverted and incubated at 37° C. in the dark for 48 hours, after which revertant colonies on control and test plates were counted.

In a separate study, UV-C (254 nm) radiation was used as the mutagen or positive control for bacterial mutation. Cells of *S. typhimurium* were irradiated with a UV-C lamp at a dose rate of approximately 1 J/m2. Mutated (exposed) cells were added immediately to 100 μl sterile water and either 100 μl plant extracts (equivalent to 100 μg) or to DMSO alone. Controls consisted of an identical set of tubes with water and extracts, but with bacterial cells not exposed to radiation. Molten agar was added to all tubes, poured on to Petri dishes with MGA and incubated at 37° C. for 48 hours.

Tumor growth and development are known to be associated with increased rates or incidents of mutation. Thus, suppression of mutation may be an acceptable measure of tumor inhibition. The mutagen 2-AA dramatically increased mutation rate based on revertant colonies formed in the presence of 2-AA, Table 3, in which the number of colonies formed (991.6) is approximately 20-fold greater than the control (48.2). The inhibition effect of the leaf extract is apparent on mutation rate is apparent in comparisons of the colonies formed with 2-AA Control C 991.6 versus 2-AA in combination of leaf, new growth rhizome, and mature rhizome 303.3, 2029, and 254.0, respectively and the corresponding percent inhibition, 73.0, 82.5, and 78.2, respectively, Table 3.

From Table 3, the inhibition effects of the *Shortia* extract are obvious and in agreement with tumor suppression result summarized in Table 1 and 2.

The preceding methods and examples are presented by way of illustration, not limitation. The invention anticipates different methods of isolation of extracts as well as different tissues and dilutions of the extracts. Thus, the broadest interpretation should be given to the appended claims.

TABLE 1

Tumor inhibition for three tissues with 4 concentrations of a plant extract.

| SAMPLE | DILUTION (CONCENTRATION) | % TUMOR INHIBITION | TISSUE MEAN |
|---|---|---|---|
| Cont | Not Applicable | -0- | |
| LF | 1:100 (10 mg/ml) | 72.6 | ~69.9 |
| LF | 1:1,000 (1 mg/ml) | 72.0 | |
| LF | 1:10,000 (0.1 mg/ml) | 74.5 | |
| LF | 1:100,000 (0.01 mg/ml) | 60.6 | |
| NRh | 1:100 (10 mg/ml) | 86.1 | ~70.0 |
| NRh | 1:1,000 (1 mg/ml) | 66.4 | |
| NRh | 1:10,000 (0.1 mg/ml) | 66.7 | |
| NRh | 1:100,000 (0.01 mg/ml) | 59.0 | |
| MRh | 1:100 (10 mg/ml) | 88.0 | ~81.8 |
| MRh | 1:1,000 (1 mg/ml) | 81.3 | |
| MRh | 1:10,000 (0.1 mg/ml) | 78.8 | |
| MRh | 1:100,000 (0.01 mg/ml) | 79.2 | |

TABLE 2

Tumor inhibition for 3 concentrations of two solvents and controls.

| EXTRACTION SOLVENT | DILUTION (CONCENTRATION) | % INHIBITION |
|---|---|---|
| HEXANE | 1:100 | 63.4 |
| HEXANE | 1:1000 | 27.8 |
| HEXANE | 1:10,000 | 17.1 |
| METHANOL | 1:100 | 63.8 |
| METHANOL | 1:1000 | 27.0 |
| METHANOL | 1:10,000 | 5.6 |
| NEG CONTROL (CAMPTOTHECIN) | 1:10,000 | 100 |

TABLE 3

Mutation inhibition for extracts from three tissues and control.

| PLANT EXTRACT | REVERTANT COLONIES WITHOUT 2-AA | REVERTANT COLONIES WITH 2-AA | % INHIBITION |
|---|---|---|---|
| CONTROL (DMSO + S9) | 48.2 | 991.6 | N/A |
| LEAF | 50.3 | 303.3 | 73.0 |
| NEW GROWTH RHIZOMES | 48.2 | 212.9 | 82.5 |
| MATURE RHIZOMES | 46.2 | 254.0 | 78.2 |

What is claimed is:

1. A solvent extract of leaf tissue of *Shortia galacifolia*, wherein the extract has anti-tumor properties; and wherein the solvent is selected from the group consisting of an aqueous mixture of ethanol, an aqueous mixture of methanol, hexane and dimethyl sulfoxide.

2. A solvent extract of rhizome tissue *Shortia galacifolia*, wherein the extract has anti-tumor properties; and wherein the solvent is selected from the group consisting of an aqueous mixture of ethanol an aqueous mixture of methanol, hexane and dimethyl sulfoxide.

* * * * *